:::

United States Patent [19]

Bonhote et al.

[11] Patent Number: 5,683,832

[45] Date of Patent: Nov. 4, 1997

[54] HYDROPHOBIC LIQUID SALTS, THE PREPARATION THEREOF AND THEIR APPLICTION IN ELECTROCHEMISTRY

[75] Inventors: Pierre Bonhote, Neuchatel; Ana-Paula Dias, Lausanne, both of Switzerland

[73] Assignee: Asulab S.A., Bienne, Switzerland

[21] Appl. No.: 574,317

[22] Filed: Dec. 18, 1995

[30] Foreign Application Priority Data

Dec. 21, 1994 [CH] Switzerland ............................ 03862/94
Dec. 27, 1994 [FR] France .................................... 94 15704

[51] Int. Cl.$^6$ .................................................. H01M 6/30
[52] U.S. Cl. ........................ 429/111; 252/62.2; 429/194; 548/335.1
[58] Field of Search ............................ 429/111, 194; 252/62.2; 548/335.1

[56] References Cited

U.S. PATENT DOCUMENTS

| 4,463,071 | 7/1984 | Gifford et al. | 429/194 |
| 4,463,072 | 7/1984 | Gifford et al. | 429/194 |
| 4,505,997 | 3/1985 | Armand et al. | 429/192 |
| 5,135,825 | 8/1992 | Mori et al. | 429/194 |

FOREIGN PATENT DOCUMENTS

| 0096629 | 12/1983 | European Pat. Off. | 429/192 |

OTHER PUBLICATIONS

Proc. –Electrochem Soc., vol. 16, 1992, pp. 386–396, E.I. Cooper et al "New, stable ambient–temperature molten salts".

*Primary Examiner*—Aaron Weisstuch
*Attorney, Agent, or Firm*—Sughrue, Mion, Zinn, Macpeak & Seas, PLLC

[57] ABSTRACT

Hydrophobic liquid salts of the general formula $$R_1-N \overset{R_2}{\underset{R_5 \quad R_4}{\diagdown\diagup}} \overset{\oplus}{N} - R_3 (CF_3SO_2)_2 N^-$$

in which $R_1$ and $R_3$ are the same or different and each represent a straight or branched chain alkyl radical, a fluoroalkyl radical or an alkoxyalkyl radical of 1 to 8 carbon atoms; and $R_2$, $R_4$, and $R_5$ are the same or different and each represent a hydrogen atom or an alkyl radical with 1 to 3 carbon atoms.

The invention has applications as an electrolyte solvent in electrochemical photovoltaic cells.

9 Claims, 1 Drawing Sheet

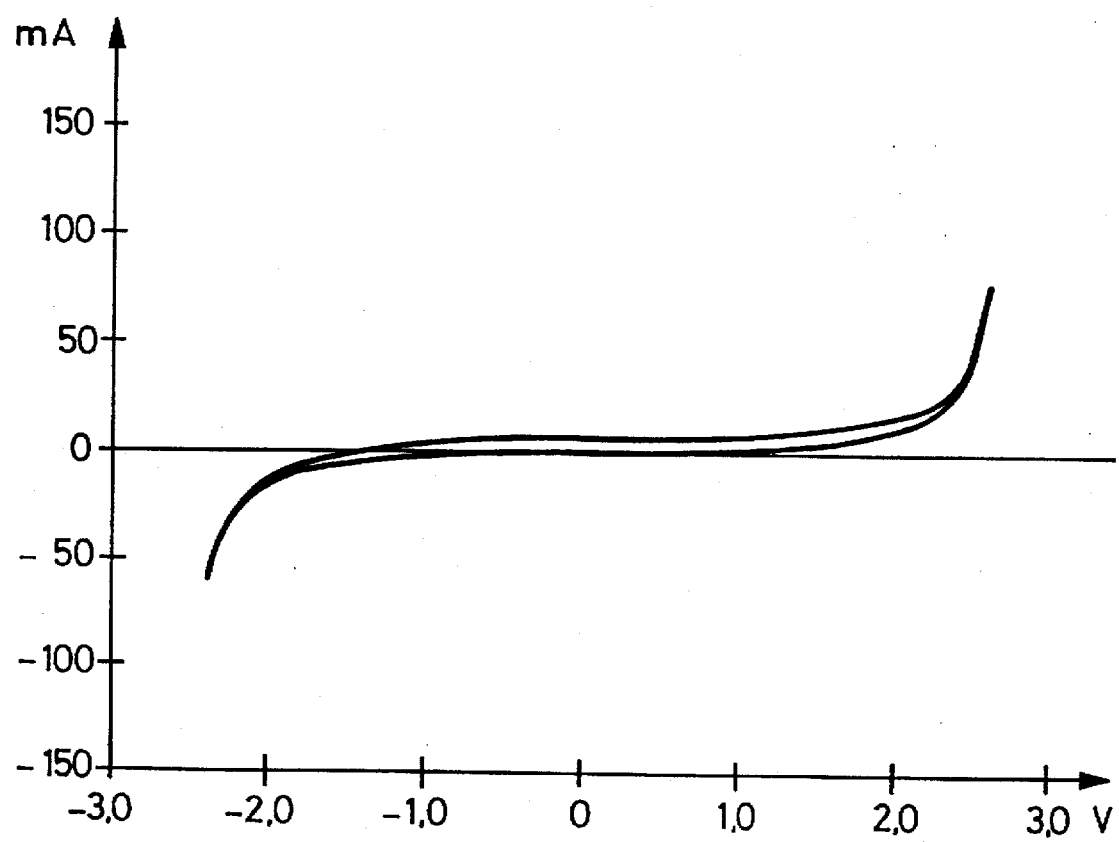

HYDROPHOBIC LIQUID SALTS, THE PREPARATION THEREOF AND THEIR APPLICTION IN ELECTROCHEMISTRY

1. Field of the Invention

It is an object of the instant invention to provide new liquid hydrophobic salts having low viscosity at ambient temperatures having an N,N'-dialkylimidazolium cation and a bis-trifluoromethane sulfonylamide $(CF_3SO_2)_2N^-$ (otherwise termed bis-triflylamide) anion, as well as a process for their manufacture.

The invention also relates to the use of said salts as hydrophobic polar solvents for electrochemical or synthetic applications, for example as a solvent in an electrolytic composition for use in electrochemical photovoltaic cells.

Salts that are liquid at ambient temperatures having a substituted imidazolium cation and trifluoromethane sulfonate anion (otherwise termed triflate) are already known. Such compounds are described in a publication by E. J. Cooper and E. J. M. O'Sullivan (The Electrochem. Soc., Proceedings Vol. 92–16 (1992)). The compounds have varying viscosities, but are all miscible with water (hydrophilic) except for dodecyl-1-ethyl-3 imidazolium triflate, which is, in fact, solid at ambient temperatures (melting point 32° C.).

2. Description of the Prior Art

U.S. Pat. No. 4,505,997 describes novel chemical compounds, namely bis-triflylamides of alkali metals obtained by ion exchange from the corresponding tetrabutyl ammonium. These salts are solid compounds for incorporation into a polymer matrix to form solid electrolytes for the production of primary or secondary electrochemical generators. These salts are, moreover, described as being strongly hydrophilic, a property which the inventors attribute substantially to the bis-triflylamide anion.

BRIEF SUMMARY OF THE INVENTION

It has now surprisingly been found that a salt composed of a substituted imidazolium cation and of a bis-triflylamide anion is liquid at ambient temperature, hydrophobic and has an only slightly elevated viscosity that favours ion mobility, relatively high conductivity, high thermal stability (at least up to 300° C.), an insignificant vapour pressure at ambient temperatures and moreover less than 0.1 mbar at 150° C., a broad electrochemical stability range (at least from −2 V to 2 V as compared with the iodo/tri-iodide couple), all these properties making it possible to use salts of this type in an advantageous manner as solvents in an electrochemical system, such as electrochemical photovoltaic cells, or for synthesis requiring aprotic polar solvents.

BRIEF DESCRIPTION OF THE INVENTION

The compounds of the invention can be represented by the following formula:

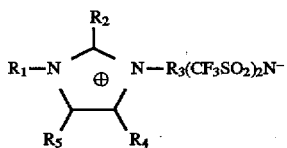

in which $R_1$ and $R_3$ are the same or different and each represents a straight or branched chain alkyl radical, a fluoroalkyl radical or an alkoxyalkyl radical with 1 to 8 carbon atoms; and $R_2$, $R_4$, and $R_5$ are the same or different and each represents a hydrogen atom or an alkyl radical with 1 to 3 carbon atoms.

$R_1$ or $R_3$ preferably represents a methyl, ethyl, butyl, isobutyl, octyl, methoxyethyl or 2,2,2-trifluoroethyl radical and $R_2$, $R_4$, and $R_5$ represent hydrogen or a methyl or ethyl radical.

The invention also relates to a process for obtaining said compounds by ion exchange in an aqueous medium between a bis-triflylamide of an alkali metal, preferably lithium, and a substituted imidazoliumhalide, preferably bromide or iodide, according to the following reaction diagram:

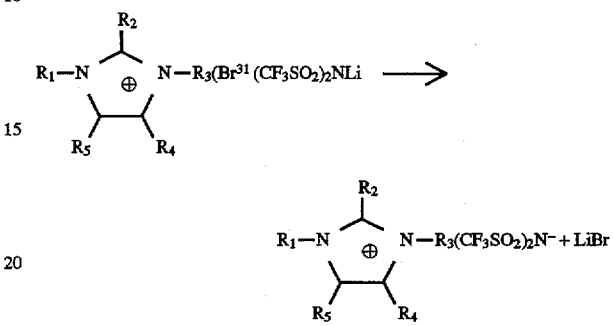

Lithium bis-triflylamide is a commercially available compound, for example, from 3M (St. Paul Minn., USA).

Bis-triflylamides of an alkali metal can also be prepared according to known processes of the prior art, such as those described in EP 0 096 629 starting from a perfluoroalkane sulfonic anhydride, or by J. R. Foropoulos and D. D. Desmarteau (Inorg. Chem. 23, (3) 720-3 723 (1984)) starting from a fluoride of perfluoroalkane sulfonic acid.

The substituted imidazolium halide is obtained using a known process by reacting an alkyl halide $R_3X$ on an imidazole suitably substituted by $R_1$, $R_2$, $R_4$, and $R_5$ in an organic solvent, with stirring.

DETAILED DESCRIPTION OF THE INVENTION

The following examples given by way of non-limiting examples describe the preparation of a certain number of compounds according to the invention, as well as their physicochemical and electrochemical properties that make them suitable for being used advantageously as an electrolytic solvent.

EXAMPLE 1

Methyl-1-butyl-3-imidazolium-bis-triflylamide 0.1 mol (8.2 g) of methyl-1-imidazole were dissolved in 200 ml of trichloroethane in a reaction vessel and a solution of 0.12 mol (16.44 g) of butyl bromide in 100 ml trichloroethane was then added dropwise at ambient temperature with vigorous stirring. The mixture was then heated under reflux for 2 hours and decanted. Methyl-1-butyl-3-imidazoliumbromide separates out in the form of a liquid. The bromide was then washed twice using 100 ml trichoroethane at 50° C., dried for one hour in a Rotavapor at 150° C. under reduced pressure of 0.1 mbar to give 15.3 g (yield 70%) of methyl-1-butyl-3-imidazoliumbromide.

50 mmol (11 g) of bromide obtained in the preceding step was then dissolved in 50 ml of water and a solution of 50 mmol (14.35 g) of lithium bis-triflylamide in 50 ml of water was added thereto in one addition. The solution immediately becomes cloudy and separates into two phases after decanting. After eliminating the supernatant aqueous phase, the liquid salt was washed twice with 50 ml water, then dried for one hour at 150° C. under reduced pressure of 0.1 mbar. This yielded 18.9 g of the product of the invention (yield 90%) as a colourless liquid non-miscible with water, having the refractive index $n_D$=1.4271. The freezing point of this liquid is less than −25° C. The hydrophobic nature of the product obtained is confirmed by Karl Fisher titration of the product previously saturated in water having a water content of only 1.4% of volume.

Measurement of the density of the compound of the invention effected at 20° C. yields a value d=1.429 g·cm$^{-3}$, and a kinetic viscosity measurement effected at 20° C. with a Haake ball microviscosimeter makes it possible to determine the value of the coefficient of viscosity η=52.4 cP.

By way of comparison, the homologous compound known from the prior art, methyl-1-butyl-3-imidazolium triflate, has a melting point of 16° C., is soluble in water, and has a viscosity of η=90 cP.

The compound of the invention was also found to have high thermal stability up to 300° C. and a very low vapour pressure (less than 0.1 mbar at 150° C.).

The conductivity of the liquid salt measured at 20° C. using an Autolab potentiostat frequency analyser has the value σ=3.88 mS·cm$^{-1}$, i.e. a value of the same order of magnitude as the triflate homolog (σ=3.68 mS·cm$^{-1}$).

The cyclovoltammogram shown in FIG. 1, taken at 20° C., with a platinum working electrode having a surface of 0.78 mm$^2$ and a reference electrode of this same metal in contact with the iodo/tri-iodide redox couple present in the same liquid salt, with a sweep of 50 mV$_s^{-1}$, shows that the compound of the invention has great electrochemical stability in the range between −2.0 V and +2.2 V.

EXAMPLE 2

Methyl-1-ethyl-3-imidazolium-bis-triflylamide

Using a two-step process similar to that of Example 1, but replacing 0.12 mol of butyl bromide by 0.25 mol (27.75 g) of ethyl bromide in the first step, 54 g (yield 78%) of the product of the invention were obtained in the form of a colourless liquid having the following physico-chemical properties:

| Freezing point | <−25° C. |
|---|---|
| Water content (Karl Fisher): | 1.4% |
| $d^{20}$ = 1.52 g · cm$^{-3}$ | η = 34.3 cP |
| $n_D$ = 1.4231 | σ = 8.84 mS · cm$^{-1}$ |

A cyclovoltammogram conducted under the same conditions as in Example 1 shows that the compound of the invention has an electrochemical range between −2.0 V and 2.2 V.

EXAMPLE 3

Ethyl-1-butyl-3-imidazolium-bis triflylamide

Proceeding as indicated in Example 1, but starting from 0.1 mol (9.6 g) ethyl-1-imidazole, 13 g (yield 60%) of the compound of the invention were obtained in the form of a colourless liquid having the following physico-chemical properties:

| Freezing point | <−25° C. |
|---|---|
| Water content (Karl Fisher): | 1.3% |
| $d^{20}$ = 1.52 g · cm$^{-3}$ | η = 47.6 cP |
| $n_D$ = 1.4285 | σ = 4.12 mS · cm$^{-1}$ |

Triflylamides of the following cations were prepared in the same manner as in Examples 1 to 3, but starting from differently substituted imidazoles:

Methyl-1-methyl-3 -imidazolium; methyl-1-methoxyethyl-3-imidazolium; methyl-1-1,2,2,2-trifluoroethyl-3-imidazolium; ethyl-1-ethyl-3-imidazolium; methyl-1-methyl-2-ethyl-3 -imidazolium; ethyl-1-methyl-2-ethyl-3-imidazolium; methyl-1-ethyl-3-methyl-5-imidazolium; ethyl-1-ethyl-3-methyl-5-imidazolium; ethyl-1-isobutyl-3-imidazolium; methyl-1-octyl-3-imidazolium.

EXAMPLE 4

An electrochemical photovoltaic cell having a hydrophobic liquid salt as electrolytic solvent An electrochemical photovoltaic cell was produced of the type described in international patent application WO94/04497, composed of two electrode assemblies 20 μm apart, one of the electrodes being covered by a nanoparticulate layer of TiO$_2$ 0.3 μm thick with cis-dithiocyanate-bis (2,2'-bipyridyl-4,4'-dicarboxylate ruthenium II) absorbed thereon as sensitiser in an amount such that the absorption of visible light is only 5% at 520 nm. The free space between the electrodes was filled with an electrolyte composed of the liquid salt of Example 1 as solvent of 10% by weight of methylhexyl imidazolium iodide and 10 mmol of iodine.

An open circuit voltage of 530 mV and a short-circuit current of 27 μA. cm$^{-2}$ were obtained under illumination corresponding to 1/100 of standard solar illumination (AM1).

Repeating the same experiment with the liquid salt of Example 2 as solvent, 10% by weight of methylhexyl imidazolium iodide and 5 mmol of iodide, an open circuit voltage of 550 mV and a short-circuit current of 25 μA. cm$^{-2}$ were obtained.

It was also noted that the hydrophobic nature of the liquid salt used as electrolytic solvent made it possible to reduce the desorption of the sensitiser of the layer of nanoparticulate TiO$_2$. Unlike many aprotic polar solvents, a liquid salt according to the invention is inert to the tri-iodide.

This example is given by way of illustration and the person skilled in the art will be able to use the hydrophobic liquid salts of the invention in other applications in the electrochemical field without departing from the scope of the invention.

We claim:

1. Hydrophobic liquid salts of the general formula $$R_1-N \underset{R_5}{\overset{R_2}{\diagdown}} \underset{R_4}{\diagup} N-R_3(CF_3SO_2)_2N^-$$

in which $R_1$ and $R_3$ are the same or different and each represent a straight or branched alkyl radical, a fluoroalkyl radical, or an alkoxyalkyl radical of 1 to 8 carbon atoms; and $R_2$, $R_4$, and $R_5$ are the same or different and each represent a hydrogen atom or an alkyl radical with 1 to 3 carbon atoms.

2. Hydrophobic liquid salts according to claim 1, characterised in that $R_1$ or $R_3$ represent a methyl, ethyl, butyl, isobutyl, octyl, methoxyethyl, or 2,2,2-trifluoroethyl radical and $R_2$, $R_4$, and $R_5$ represent hydrogen or a methyl or ethyl radical.

3. A hydrophobic liquid salt according to claim 1, characterised in that it corresponds to methyl-1-butyl-3-imidazolium-bis-triflylamide.

4. A hydrophobic liquid salt according to claim 1, characterised in that it corresponds to methyl-1-ethyl-3-imidazolium-bis-triflylamide.

5. A hydrophobic liquid salt according to claim 1, characterised in that it corresponds to ethyl-1-butyl-3-imidazolium-bis-triflylamide.

6. A process for the preparation of a hydrophobic liquid salt of the general formula

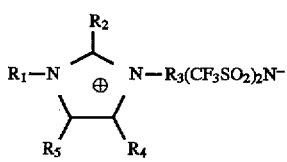

in which $R_1$ and $R_3$ are the same or different and each represent a straight or branched alkyl radical a fluoroalkyl radical, or an alkoxyallcyl radical of 1 to 8 carbon atoms; and $R_2$, $R_4$ and $R_5$ are the same or different and each represent a hydrogen atom or an alkyl radical with 1 to 3 carbon atoms; said process being characterized in that an imidazolium halide substituted by $R_1$, $R_2$, $R_3$, $R_4$, and $R_5$ is caused to react in aqueous medium with an alkali metal-bis-triflylamide, and in that the product obtained is separated by decantation.

7. A process of preparation according to claim 6, characterised in that the halide is a bromide or an iodide and the alkali metal is lithium.

8. An electrolytic composition containing as an aprotic polar solvent a hydrophobic liquid salt of the general formula

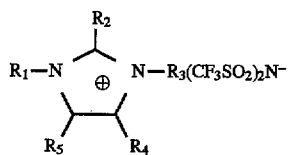

in which $R_1$ represents an alkyl radical having 1 to 5 carbon atoms, $R_3$ represents a straight or branched alkyl radical, a fluoroalkyl radical, or an alkoxyalkyl radical having 1 to 8 carbon atoms; and $R_2$, $R_4$, and $R_5$ each represent a hydrogen atom or an alkyl radical having 1 to 3 carbon atoms.

9. An electrochemical photovoltaic cell comprising an electrolytic composition according to claim 8 containing the iodo/tri-iodide redox couple.

* * * * *

UNITED STATES PATENT AND TRADEMARK OFFICE
CERTIFICATE OF CORRECTION

PATENT NO. : 5,683,832
DATED : November 4, 1997
INVENTOR(S) : Bonhote et al.

It is certified that error appears in the above-identified patent and that said Letters Patent is hereby corrected as shown below:

Title page,
Item [75], Inventors, should read as follows:
-- [75] Inventors: Pierre Bonhote, Neuchatel; Ana-Paula Dias, Lausanne, both of Switzerland; Michel Armand of Montreal, Québec, Canada --

Signed and Sealed this

Eighth Day of June, 2004

JON W. DUDAS
*Acting Director of the United States Patent and Trademark Office*